United States Patent [19]

Sanford et al.

[11] 4,103,177

[45] Jul. 25, 1978

[54] SURFACE QUALITY ANALYSIS

[75] Inventors: Richard A. Sanford; Edwin K. Clardy, both of Bartlesville, Okla.

[73] Assignee: Phillips Petroleum Company, Bartlesville, Okla.

[21] Appl. No.: 636,490

[22] Filed: Dec. 1, 1975

[51] Int. Cl.² ................... G01N 21/30; G01N 21/32
[52] U.S. Cl. ................................. 250/562; 356/200; 356/238; 250/572
[58] Field of Search ............... 250/562, 563, 559, 572, 250/571, 224, 214 R, 206; 356/237–239, 199, 200; 328/128

[56] References Cited

U.S. PATENT DOCUMENTS

| | | | |
|---|---|---|---|
| 3,065,615 | 11/1962 | Abrams | 356/238 |
| 3,283,162 | 11/1966 | Quittner | 356/200 |
| 3,388,261 | 6/1968 | Roberts et al. | 356/238 |
| 3,494,236 | 2/1970 | Kono et al. | 250/559 |
| 3,534,402 | 10/1970 | Crowell et al. | 250/571 |
| 3,729,635 | 4/1973 | Shottenfeld | 250/562 |
| 3,781,117 | 12/1973 | Laycak et al. | 356/200 |
| 3,841,761 | 10/1974 | Selgin | 250/562 |
| 3,892,492 | 7/1975 | Eichenberger | 250/571 |

FOREIGN PATENT DOCUMENTS 996,366  6/1965  United Kingdom ................. 250/219

Primary Examiner—Alfred E. Smith
Assistant Examiner—David K. Moore

[57] ABSTRACT

Analysis of the reflectance characteristics of a surface such as a sample of knitted fabric utilizes one or more photosensitive detector means to scan the surface and to automatically produce at least one surface quality signal in response to the reflective characteristics of the surface. In preferred embodiments of the invention a modulated light source is used to illuminate the surface in order to minimize the effect of ambient lighting conditions, and a plurality of detector means are used to obtain a more accurate representation of the quality of the surface being scanned.

61 Claims, 9 Drawing Figures

SURFACE QUALITY ANALYSIS

This invention relates to a method and apparatus for determining the reflectance characteristics of a surface. In another aspect the invention relates to a method and apparatus for determining the reflectance characteristics of a fabric sample. In yet another aspect the invention relates to a method and apparatus for minimizing the effect of ambient lighting conditions in the determination of the reflective characteristics of a surface. In still another aspect the invention relates to a method and apparatus for using a plurality of detectors to determine the reflective characteristics of a surface. In another aspect the invention relates to a method and apparatus for producing a surface quality signal, representative of the reflective characteristics of a surface, which correlates well with human observance of the surface. In still another aspect, the invention relates to a method and apparatus for producing a surface quality signal comprising those reflective characteristics of a surface which are more readily observed by the human eye.

An important problem in many industries is that of evaluating uniformity of production of items such as fiber, yarn, paper products, and other similar material which are either produced having a surface which will affect the quality of the finished product or which are intended to be used in the production of such surfaces. The problem is particularly acute in those situations where certain irregularities or defects in the basic product will not become apparent until some subsequent processing step such as dyeing is accomplished. In the fine denier fibers industry, for example, nonuniformities in fibers and yarns will become apparent later in the knitted or woven fabric that is to be the final product. One important characteristic of yarns is the ability to take dye uniformly. Color density variations caused by yarn nonuniformities which affect dye uptake will greatly affect the value of the yarn. Evaluation of such yarn tests for color density variations can be performed on long test sleeves which are circular knitted using the yarn to be tested and are then dyed with a sensitive test dye. Such a sleeve can be comprised of several sections each containing a test yarn which is a sample of some larger unit of yarn production.

The two primary types of variations which are of interest in determining the quality of a fabric surface are long term variations which occur between spinning or finishing machines or from day to day as machine settings vary and which may be observed as differences between different fabricated samples, and short term variations which occur within a single test section. The short term variations may appear as changes in color density that occur within one or a few courses of knitting on a sleeve. The most transient type of defect usually extends for less than one inch along a single course of a sleeve and is usually darker than the surrounding material. This type of defect is given a descriptive name such as dark flashes or dark dye defects. Most other dye uptake defects within a fabric will extend for one to a hundred or more full courses of knitting and are referred to, generally, as streaks. The edges of a streak may be either sharp or diffuse. If there is a definite periodicity to the pattern of streaks in a sample section, the streaks are referred to as Barre.

Since the quality and therefore the value of a fabric is generally determined in part by its appearance to the human eye, human observance of test samples is commonly used to evaluate the surface qualities of the sample. Such subjective evaluations are made by laboratory personnel who view each sleeve section and make a quality evaluation based on experience and/or laboratory standards. The results may be reported only as good or bad, or they may include qualifiers or numerical ratings on some arbitrary scale. The evaluators may also report an alert to denote the presence of a few high contrast streaks which would make the yarn unacceptable, even in the absence of other defects.

It is therefore an object of the invention to provide a method and apparatus for determining the reflectance characteristics of a surface. Another object of the invention is to provide a method and apparatus for determining the reflectance characteristics of a fabric sample. Yet another object of the invention is to provide a method and apparatus for minimizing the effect of ambient lighting conditions in the determination of the reflective characteristics of a surface. Still another object of the invention is to provide a method and apparatus for using a plurality of detectors to determine the reflective characteristics of a surface. Another object of the invention is to provide a method and apparatus for producing a surface quality signal, representative of the reflective characteristics of a surface, which correlates well with human observance of the surface. Still another object of the invention is to provide a method and apparatus for producing a surface quality signal comprising those reflective characteristics of a surface which are more readily observed by the human eye.

In accordance with the invention the surface of a sample to be tested is observed by illuminating the surface and by scanning the surface with at least one photosensitive detector to generate a surface quality signal representative of the reflective characteristics of the surface. In order to minimize the effects of ambient lighting conditions on the surface quality signal, the light source illuminating the surface can be a modulated light source with demodulation of the detector signal being used to obtain a reflectance signal which is generally independent of changes in ambient lighting. In order to produce a more accurate surface quality signal, a plurality of photosensitive detectors can be used with the detector signals being combined in various ways to place certain defects observed by only one or a few of the total number of detectors in proper perspective. When a plurality of detectors are arranged in a suitable array, the method and apparatus of the invention can be utilized to discriminate in favor of or against certain types of variations. Such an array particularly suited for use with analysis of knitted yarn samples is a straight line oriented generally perpendicular to the scanning direction so that correlation of signals from the various detectors will readily yield information relating to the dark dye defects, streaks, and other similar variations which manifest themselves as a change in color intensity extending across the width of the sample surface.

In addition to scanning a surface to observe general and/or specific variations in reflectance from the surface, the method and apparatus of the invention can be utilized to produce a surface quality signal which ignores minor variations which would not be observed by the human eye or performs other such discriminatory functions such as separately observing or counting substantial variations which, although few in number, might nonetheless be particularly objectionable. In accordance with the invention changes in reflectance from the surface being scanned can be analyzed regardless of whether the change represents an increase or decrease in reflected light so that light streaks and dark streaks can both be observed equally.

Other objects and advantages of the invention will be apparent from the specification and claims and from the detailed description of the drawing in which:

Figure 1:
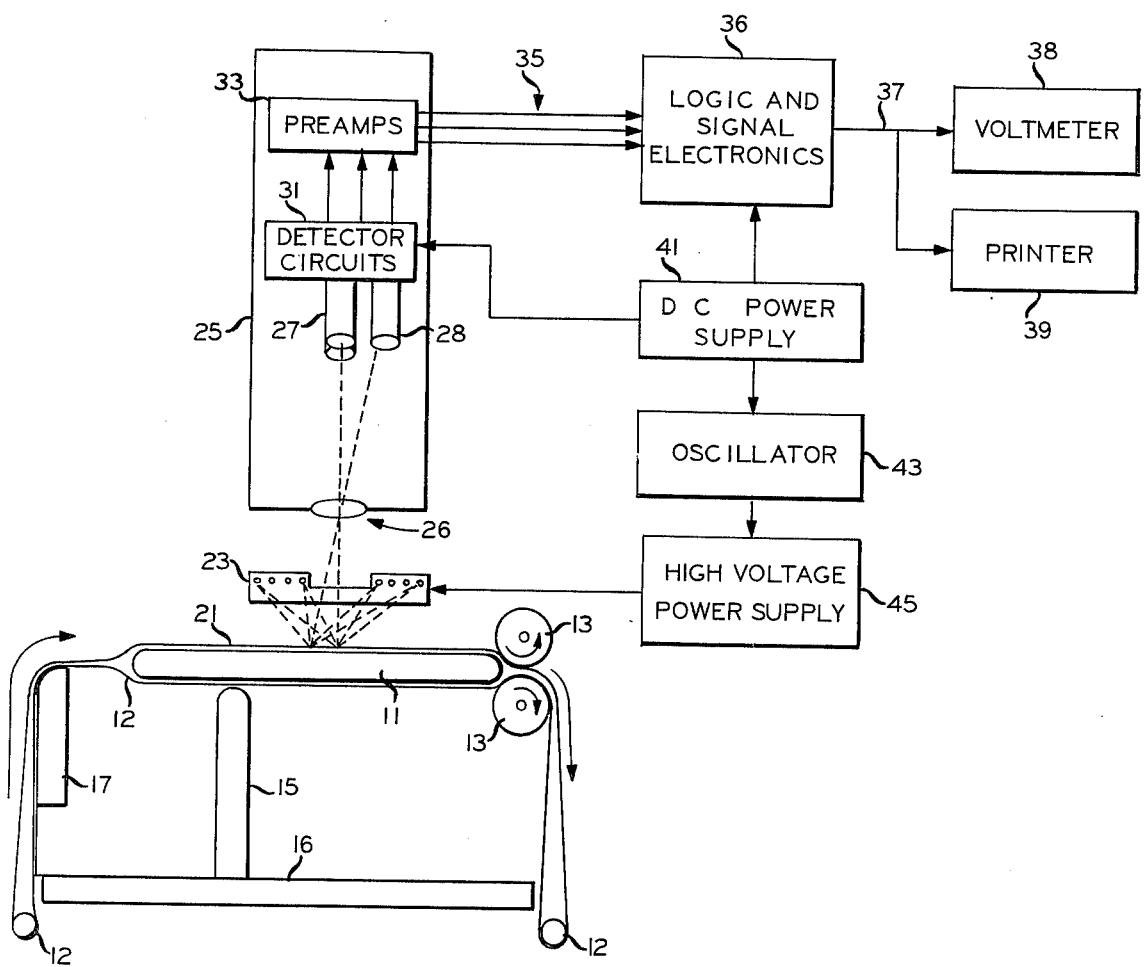
FIG. 1 is a schematic representation of the scanning apparatus of the invention with a schematic block diagram of the apparatus associated therewith.

Referring now to FIG. 1 there is illustrated a mandrel 11 which has been inserted into a sleeve 12, the sleeve 12 having been prepared in any suitable manner such as by circular knitting of a yarn to be tested, followed by dyeing of the knitted sleeve in a test dye material. A pair of opposed rollers 13 which are driven by any suitable means, such as an electric motor (not shown), contact the sleeve to draw the sleeve 12 over the mandrel 11 and between the rollers 13. The spacing of the rollers 13 and the shaping of the end of the mandrel 11 adjacent thereto is such that the mandrel is not drawn between the rollers but is repelled by the rollers and is maintained with one end adjacent the rollers as illustrated. The end of the mandrel 11 adjacent the rollers 13 is therefore supported by the sleeve 12 which is in turn supported by the pressure of the rollers 13. The opposite end of the mandrel 11 is supported by a fulcrum 15 which is in turn attached to any suitable surface 16 such as a table or other similar support. The portion of the fulcrum 15 contacting the sleeve 12 is preferably sufficiently smooth to permit support of the mandrel 11 through the sleeve 12 without interference with the relative movement of the sleeve over the mandrel. A suitable guide 17 can be utilized to align the sleeve 12 for passage over the mandrel 11. A preferred mandrel 11 is one having an elongated flattened shape with a length and width substantially in excess of its thickness, the thickness of the mandrel being illustrated by the cross section of FIG. 1. The ends are rounded from top to bottom as illustrated and are also preferably rounded from side to side in order to provide smooth advancement of the mandrel through the sleeve. A particularly preferred mandrel is constructed of polyethylene or other similar smooth material which presents a minimum of frictional engagement with the sleeve 12.

In operation, therefore, the mandrel 11 extends and slightly stretches the sleeve 12 to provide a flat upper surface 21 of the sleeve 12 which can be analyzed in accordance with the invention. A light source 23 illuminates the portion of the surface 21 to be observed. The light source 23 can be any suitable lighting means. A preferred light source is a ring lamp having one or more generally annular lamps with detection of the reflectance from the surface 21 being accomplished through an opening in the center of the annular lighting means.

A detector assembly 25 is supported by suitable means (not shown) for maintaining the detector assembly 25 in a fixed relationship to the lighting means 23. The detector assembly 25 supports a lens 26 and contains at least one detector means 27 for converting a portion of the light transmitted through the lens 26 to an electronic signal. In the preferred embodiment illustrated a plurality of detector means 27 are positioned in an array such that the light impinging on the operative surfaces of the detector means 27 is representative of the reflection from a straight line on the surface 21, the straight line of the surface 21 being generally perpendicular to the direction of relative motion between the surface 21 and the detector means 27. In addition, a reference detector 28 can be utilized to initiate and/or terminate operation of the detectors 27 by sensing a marking code or other similar feature on the surface 21 to provide automatic scanning of separate preselected portions of the sleeve 12. Although many different numbers and arrangements of detectors can be used in accordance with the invention, it is preferred that the operative surface of each detector be located substantially at the focal plane of the lens 26 in order to provide the desired degree of resolution. Depending on the surface to be observed, the focal length of the lens 26 and accordingly the resolution provided by the detectors 27 should be adequate to provide a distinct signal in response to the smallest variation which can be of possible significance with regard to the quality of each surface 21. In the case of a knitted sample, each detector is preferably capable of viewing an area equal in width to about the width of one course of knitting.

Individual detector circuits 31 and preamplifier circuits 33 are preferably located within the detector assembly 25 to provide preamplified detector signals 35 to the logic and signal electronics 36. The logic and signal electronics 36 in turn provide at least one surface quality signal 37 for observation by a machine operator or for recording to produce a permanent record. Suitable output equipment such as a conventional or digital voltmeter 38 or a printer 39 can be used for observing and/or storing the surface quality signal 37. A suitable power supply such as a DC power supply 41 provides operating power to the circuits of the apparatus.

A high voltage power supply 45 providing operating power to the lighting means 23 is preferably modulated by the output from an oscillator 43 in order to provide a modulated light output from the lighting means 23. Proper choice of a suitable frequency for the oscillator 43 can be used to provide the analysis apparatus with a light source which will permit interference from ambient lighting changes to be ignored with the reflectance signals used in the production of the surface quality signal 37 being substantially limited to reflectance from the light means 23. For example, in a room or laboratory ordinarily lighted with incandescent and/or fluorescent light operating on 60 Hertz electrical power, an oscillator frequency of about 90 Hertz is normally preferred since it is possible to use filtering techniques to essentially ignore any 60 Hertz or 120 Hertz variations seen by the detector means 27. It can readily be seen, however, that other suitable frequencies can be used. In this same situation, the frequency of the oscillator 43 might range from about 70 to about 110 Hertz or could be elevated to any of a number of higher suitable frequency such as about 1000 Hertz. Similarly, with ambient lighting disturbances resulting from a 50 Hertz power source a choice of about 70 Hertz as the oscillator frequency would correspond to the choice of about 90 Hertz for use with a 60 Hertz power source. In other individual circumstances which may vary from one application to another, special lighting conditions may make it desirable to choose still other frequencies for the oscillator 43. Whatever the exact circumstances, the frequency for the oscillator 43 should be chosen to be as far as possible from the frequencies of any interfering light sources present and multiples of such possibly interfering frequencies.

Figure 2:
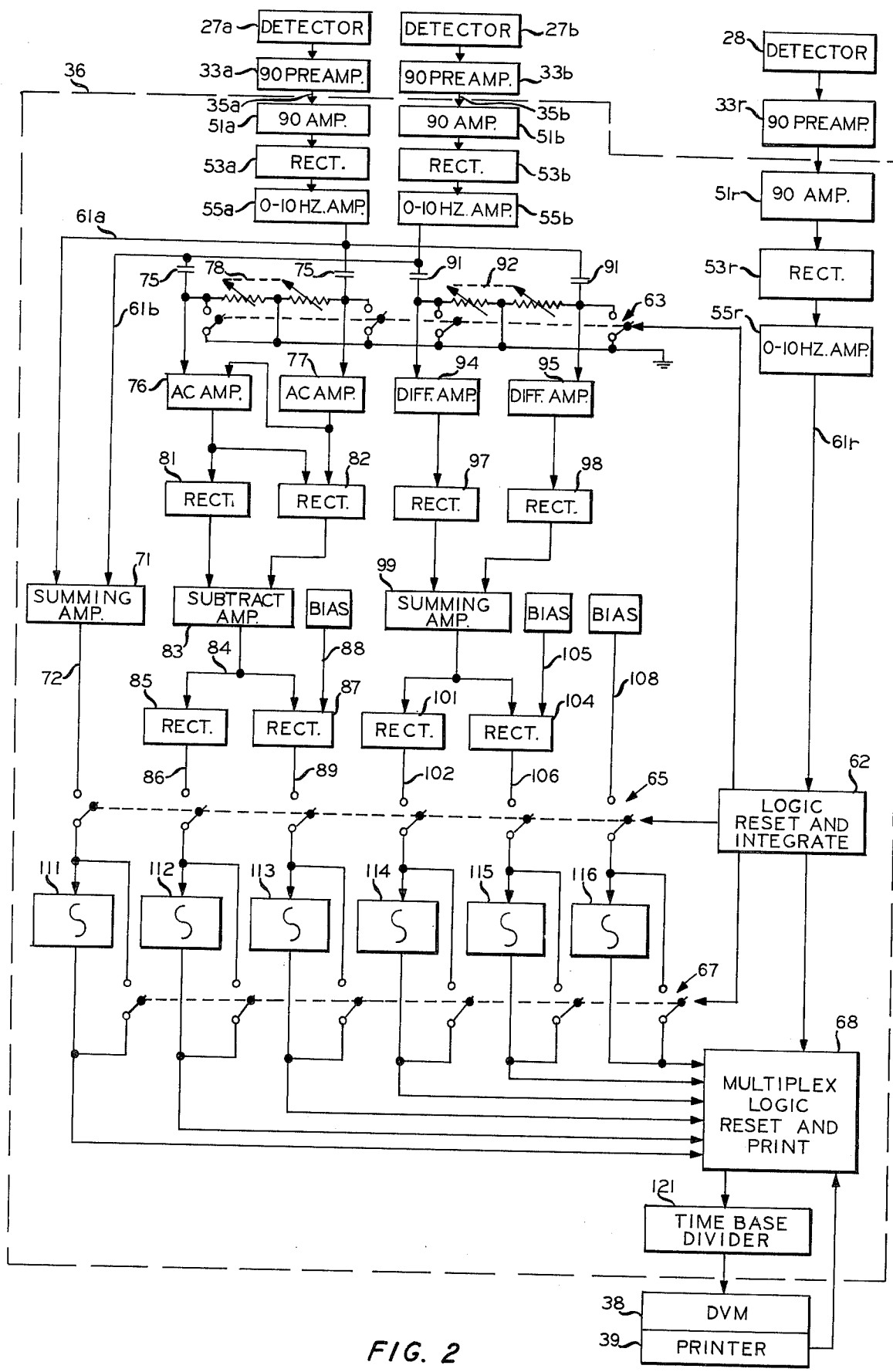
FIG. 2 is a schematic block diagram of a preferred embodiment of the logic and signal electronics of the invention.

A preferred schematic block diagram for the logic and signal electronics 36 is illustrated by FIG. 2. Associated with each detector 27a, 27b is a 90 Hertz preamplifier 33a, 33b providing detector signals 35a, 35b to respective 90 Hertz amplifiers 51a, 51b. Amplified detector signals are received from the amplifiers 51a, 51b by demodulating circuits each comprising a full wave rectifier 53a, 53b followed by a low band-pass 0–10 Hertz amplifier 55a, 55b. The preamplifiers 33a, 33b and amplifiers 51a, 51b are preferably selected to discriminate against frequencies other than the frequency of the modulated light source illuminating the surface 21. The effective band width of the low band-pass amplifiers 55a, 55b is preferably selected so that, considering the size of the smallest variation which is desirably observed on the surface 21 and the speed at which the rollers 13 are rotated, the change in detector signal represented by the smallest surface variation which is desired to be observed will be of a low enough frequency to be passed by the amplifier 55a, 55b. The detector signals 35a, 35b represent amplitude modulated, constant-frequency signals at a frequency which is determined by the frequency of the oscillator 43 with the full wave rectifier 53a, 53b and low band pass amplifier 55a, 55b affecting demodulation of the amplitude modulated signal.

The output signals from the low band pass amplifiers 55a, 55b provide reflectance signals 61a, 61b associated with respective detectors 27a, 27b. In a similar manner a reference detector reflectance signal 61r is provided by the reference detector 28 utilizing a preamplifier 33r, amplifier 51r, full wave rectifier 53r, and low band pass amplifier 55r. The reference reflectance signal 61r can be provided as an input to any suitable logic circuitry 62 which will in turn control the operation of switching means 63, 65, and 67 as well as output equipment such as a multiplex logic circuit 68 and any other desired circuitry which can be controlled in response to any reference reflectance signal 61r of relative large voltage and short duration caused by, for example, the movement of a contrasting "end of section" band on the surface 21 of the sleeve 12 past the view of the reference detector 28. Although many different logic control systems can be utilized, a presently preferred system is one in which a contrasting color line is interposed between each segment of a sleeve 12 containing a plurality of sequential segments to be tested. Once the sleeve has been positioned on the mandrel and operation of the test apparatus has been initiated, testing will continue automatically until the end of the test sleeve has been reached.

Each time a contrasting color band is detected by the reference detector 28 the output circuits such as the multiplex logic circuit 68 will be actuated to print out and/or display the one or more surface quality signals which have been generated and switch means 63, 65, 67 and any other required switching means are actuated to establish the desired zero or initial conditions in preparation for scanning of a subsequent sample. During the time that the output and initialization procedures are taking place, the contrasting segment of the sleeve passes the detector means 27a, 27b and, upon completion of the output and initialization procedures, switches 63, 65, and 67 can again be actuated to begin scanning of the succeeding sample. In this manner the contrasting portions of the sleeve, while providing a useful signal to the control circuitry of the apparatus, do not enter into the determination of surface quality since the analytical portion of the circuitry is in the process of being reset as the contrasting portion passes the view of the array formed by the detectors 27a, 27b.

The reflectance signals 61a, 61b are provided as inputs to a summing amplifier 71 which generates a total reflectance signal 72 representative of the total reflectance observed by the detectors 27a, 27b. Such a summing amplifier 71 can accept reflectance signals from any number of detectors and produce a total reflectance signal 72 representative of the sum of all reflectance signals provided thereto. The reflectance signals 61a, 61b are coupled to the inputs of two AC amplifiers 76, 77 by capacitors 75. A pair of ganged variable resistors 78 are connected between the amplifier inputs and ground in order to provide scaling of the input signals to the amplifiers 76, 77. Coupling of the output of the AC amplifier 77 to the input of the AC amplifier 76 along with use of the output of amplifier 76 as an input to a full wave rectifier 81 and use of the outputs of both amplifiers 76 and 77 as inputs to a full wave rectifier 82 can be used to result in the full wave rectifier 81 having an output which is equal to the absolute value of the sum of the capacitor coupled inputs to amplifier 76 and 77 whereas the output of the full wave rectifier 82 will be representative of the absolute value of the difference between the capacitor coupled input signals to the amplifiers 76 and 77. These output signals from the full wave rectifiers 81, 82 are provided to a subtracting amplifier 83 which produces an output signal representative of the difference between the output signal of the full wave rectifier 81 and the output signal of the full wave rectifier 82.

When the output signal 84 from the subtracting amplifier 83 is subjected to half wave rectification by a half wave rectifier 85, the output signal 86 of the half wave rectifier 85 will be equal in magnitude to the smaller of the capacitor coupled input signals to the amplifier 76 and 77 when these amplifier input signals are of the same polarity and will be equal to zero when the capacitance coupled amplifier input signals are of opposite polarity. Expressed in other terms, signal 86 can be represented by the expression $$(|A + B| - |B - A|) \geq 0$$

where A represents the capacitor coupled input signal to AC amplifier 77 and B represents the capacitance coupled input signal to the AC amplifier 76. A half wave rectifier 87 utilizing the output of the subtracting amplifier 83 and a constant bias signal 88 as inputs thereto produces an output signal 89 which is similar in form to the signal 86 but which is reduced by an amount represented by the bias signal 88 to provide a weighted version of the signal 86. Depending upon the value of the bias signal 88, the weighted signal 89 can be used to represent only those defects which are large enough to be observed by casual human observance or can be representative of those defects which are of such an intensity as to make the entire sample unacceptable. Signal 89 will, in general, be representative of the amount by which signal 86 exceeds the constant bias signal 88.

Where a different number of detectors is utilized, similar or equivalent apparatus can be utilized to produce signals equivalent to signals 86 and 89 whereby the discriminatory signal produced will be representative of the magnitude of the smallest of the capacitance coupled amplifier input signals having a like polarity when at least a preselected majority number of such input signals are of said like polarity and which is equal to zero when less than a preselected majority number of the AC amplifier input signals are of like polarity. The value of a discriminatory signal 86 or weighted discriminatory signal 89 is that it produces a response only when a preselected majority number of detectors have sensed a particular reflectance variation thereby making it possible to ignore isolated variations which may be viewed by a small percentage of the detectors. Rather than using AC coupled amplifiers as the initial amplifiers in the circuits producing the discriminatory signal 86 and weighted discriminatory signal 89, differential signal inputs representing the rate of change of the reflectance signals could be utilized as inputs to produce a similar result based on rate of change of reflectance.

Reflectance signals 61a and 61b are coupled by capacitors 91 to the inputs of two differential amplifiers 94, 95. A ganged pair of variable resistors 92 connecting the inputs of the amplifiers 94, 95 to ground provide scaling of the amplifier inputs. Each differential amplifier 94, 95 delivers a signal representative of the rate of change of the input thereto with respect to time to a respective full wave rectifier 97, 98. The outputs of the full wave rectifiers are accepted as inputs to a summing amplifier 99 which produces an output signal representative of the sum of the input signals provided thereto. A half wave rectifier 101 accepts the output of the summing amplifier 99 and produces a total absolute value signal 102 representative of the sum of the magnitudes of the outputs of differential amplifiers 94 and 95. Another half wave rectifier 104 accepts as inputs the output of the summing amplifier 99 and a constant bias signal 105 and produces in response thereto a weighted total absolute value signal 106 representative of the amount by which the total absolute value signal 102 exceeds the constant bias signal 105. In systems employing a different number of detectors 27, a differential amplifier and full wave rectifier will be associated with each detector of the system with the summing amplifier 99 accepting the outputs of all full wave rectifiers so employed as input signals thereto. Unlike discriminatory signal 86 and weighted discriminatory signal 89, the total absolute value signal 102 and weighted total absolute value signal 106 do not discriminate in favor of or against any particular type of reflectance variation. Instead, the magnitude of each variation in the derivative signal generated by the differential amplifiers 94, 95 will be given equal value regardless of how many or few of the detectors employed detect the rate of variation in question. The use of derivative or differential signals as inputs from which a weighted total absolute value signal 106 is generated make it possible to incorporate into signal 106 only those rates of change in surface reflective characteristics which are rapid enough to be observed by the human eye or to view only those rates of change in reflective characteristics which would indicate an objectionable or unsatisfactory surface characteristic regardless of the condition of the remainder of the sample surface. The value of the constant bias signal 105 can be selected to provide either such condition or to select a threshhold of total variation rate to be observed for any of a number of other purposes.

Numerous other variations and combinations of signals representing the reflective characteristics of the surface 21 can be generated in accordance with the invention. In addition, constant signals such as a constant bias signal 108 can be generated for use as reference signals or for other appropriate purposes.

In a presently preferred embodiment of the invention a plurality of integrators 111, 112, 113, 114, 115, 116 are provided. The characteristics of each such integrator are such that it adds or integrates with respect to time the input signal which is provided thereto and delivers an output signal representative of the result of that integration.

During the scanning of a sample, the switch means 63 is in the open position illustrated, and the switch means 65 is in a closed position in order to deliver the respective signals 72, 86, 89, 102, 106 and 108 to amplifiers 111, 112, 113, 114, 115, and 116. Switch means 67 is in the open position illustrated. As the approach of the end of a surface sample is communicated to the logic circuit 62 the switch means 65 disconnects the integrators from the input signals, and other appropriate action such as grounding of the inputs of the integrators may be taken in order to insure maintenance of each integrator output at the value it exhibits at the time the switch means 65 is opened. The multiplex logic circuit 68 then sequentially delivers each of the integrator output signals to a divider circuit 121 which in turn sequentially divides each integrator output signal by the time of integration. The time base divider circuit output signals to the digital volt meter 38 and printer 39 will therefore be averages, independent of the scan time or length of the sleeve sections being scanned. The time of integration can be determined by the output of the integrator 116 which, having integrated a constant bias signal 108 over the period of scanning time, will always provide an output signal representative of the length of scanning time. If this system is used, the output of the integrator 116 can be the first signal delivered to the time base divider 121 and can then be stored by the time base divider 121 for use as a time base signal by which all other integration signals will be divided. If desired, a separate timing circuit can be utilized in the time base divider 121 and the output of the integrator 116 can be used as a check to insure that the time of integration has been properly determined. Upon completion of delivery of all integrator output signals to the time base divider 121 by the multiplex logic circuit 68, the switch means 67 will be closed in order to reset the integrators to zero in preparation for receiving signals generated by scanning a subsequent surface sample. During the time that the multiplexing and integrator resetting is occuring, the switch means 63 can also be closed to ground the inputs to the AC amplifiers 76, 77 and the differential amplifiers 94, 95 so that upon initiation of a subsequent scanning sequence the inputs of all circuits will be properly zeroed or initialized. In conjunction with the operation of equipment such as the printer 39 which requires a relatively long period of time to perform its required function when compared with the length of time required by a multiplexer to deliver information thereto, a signal from the printer back to the multiplex logic circuit 68 may be utilized to insure that sequential printing of the data received is completed prior to transmission of subsequent data from the multiplexer 68 to the time base divider 121. After a sufficient time for all data to have been received and displayed by the digital volt meter 38 and the printer 39, or upon receipt of a signal (not shown) from the multiplexer to the logic circuit 62, and after the lapse of an amount of time sufficient for the contrasting segment of the test surface to have passed beneath the view of the detectors 27a, 27b, switch means 62 will be opened, switch means 65 will be closed, and switch means 67 will be opened, and the scanning process will be repeated to analyze the reflective characteristics of a subsequent surface sample.

Figure 3:
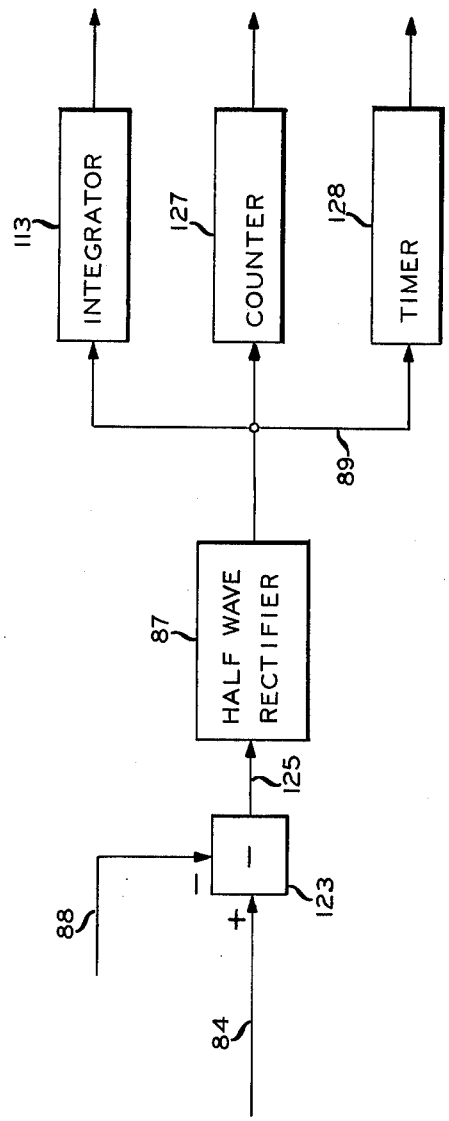
FIG. 3 is a schematic block diagram of a typical alternative embodiment of a portion of the diagram of FIG. 2.

Since the sleeve to be analyzed and the individual sample portions within the sleeves will ordinarily vary in length, the integration of each of the surface quality signals followed by dividing each integrated signal by the time of integration will provide data which can be readily compared regardless of the specific length of sample viewed. In order to isolate specific defects, however, a substantial number of additional methods can be used. For example, the outputs of one or more AC amplifiers, 76, 77 or differentiating amplifiers 94, 95 can be used to drive a strip chart recorder or other suitable instrument in order to provide a graphical representation of the streaks or dye defects observed in the sample. Such an output permits the observation of periodicity in the reflective characteristics of the sample and can be of considerable aid in identifying the production problem that caused the sample variations. Many other uses of the surface quality signals generated within the logic and signal electronics circuits 36 can also assist in obtaining desired information. As illustrated by FIG. 3, for example, the output signal 84 from the subtracting amplifier 83 and the constant bias signal 88 can be provided to a subtracting means 123 which will in turn deliver a signal 125 representative of the difference between the signals 84 and 88 to the half wave rectifier 87. The resulting discriminatory signal 89 can then be provided to the integrator 113 as illustrated by both FIGS. 2 and 3 or could be provided to a counter 127 as illustrated by FIG. 3 so that the number of instances of the signal 84 exceeding the signal 88 could be counted in any suitable manner, or could be provided to a timer 128 which could measure the length of time between successive pulses in the discriminatory signal 89, keep track of the longest or shortest time between successive pulses, keep track of the total amount of time which the signal is equal to zero, or a number of other similar uses which would be productive of information helpful in determining various surface quality characteristics of the sample and/or correcting the production problems which cause the errors. The output signals from a counter 127 and a timer 128 could then be provided to the time base divider 121 by the multiplex logic circuit 68, as is the output of the integrator 113, in order to obtain information such as defects per unit length of the sample from the counter 127 or information such as the percentage of defective length or defect-free length from the signal received from the timer 128.

Figure 4:
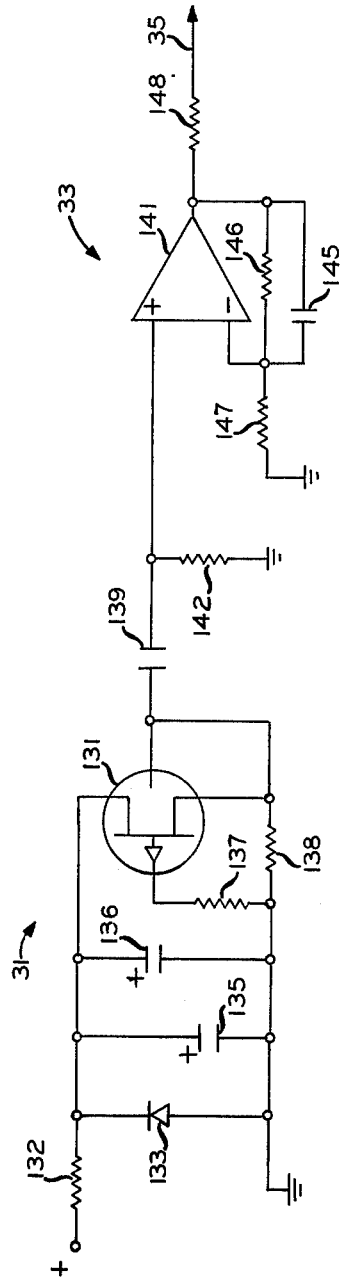
FIG. 4 is a schematic block diagram of a preferred detector and preamplifier circuit for use with the invention.

Specific preferred circuits for implementing the invention are illustrated by FIGS. 4–9. FIG. 4 illustrates a preferred detector circuit 31 and preamplifier circuit 33 for use with analysis apparatus utilizing a modulated light source. A photosensitive field effect transistor 131 is connected so that a positive supply voltage is applied through a resistor 132 to its drain terminal. A diode 133 is connected between the drain terminal and ground with the anode of the diode 133 being connected to ground and the cathode being connected to the drain terminal. In a similar manner a pair of polar capacitors 135 and 136 are connected between the drain terminal and ground with the positive side of each capacitor connected to the drain terminal. The gate terminal is connected through a resistor 137 to ground. The case and source terminals are connected to each other, are connected to ground through a resistor 138 and are connected to one terminal of a coupling capacitor 139. The case and source terminals of the photosensitive device 131 therefore comprise the output of the device which is coupled through the coupling capacitor 139 to the noninverting input terminal of an operational amplifier 141. The noninverting input terminal of the amplifier 141 is also connected through a resistor 142 to ground. The output of the operational amplifier 141 is applied through the parallel combination of a capacitor 145 and a resistor 146 to the inverting input terminal of the amplifier 141, the inverting terminal of the amplifier also being connected through a resistor 147 to ground. The output of the operational amplifier 141 is applied through a resistor 148 to provide a preamplified detector output signal 35. When a plurality of such detector and preamplifier circuits are utilized in conjunction with the apparatus of the invention, it is preferred that, to the extent possible in view of the practicalities of circuit construction, all detector circuits 31 and preamplifier circuits 33 be substantially identical.

Figure 5:
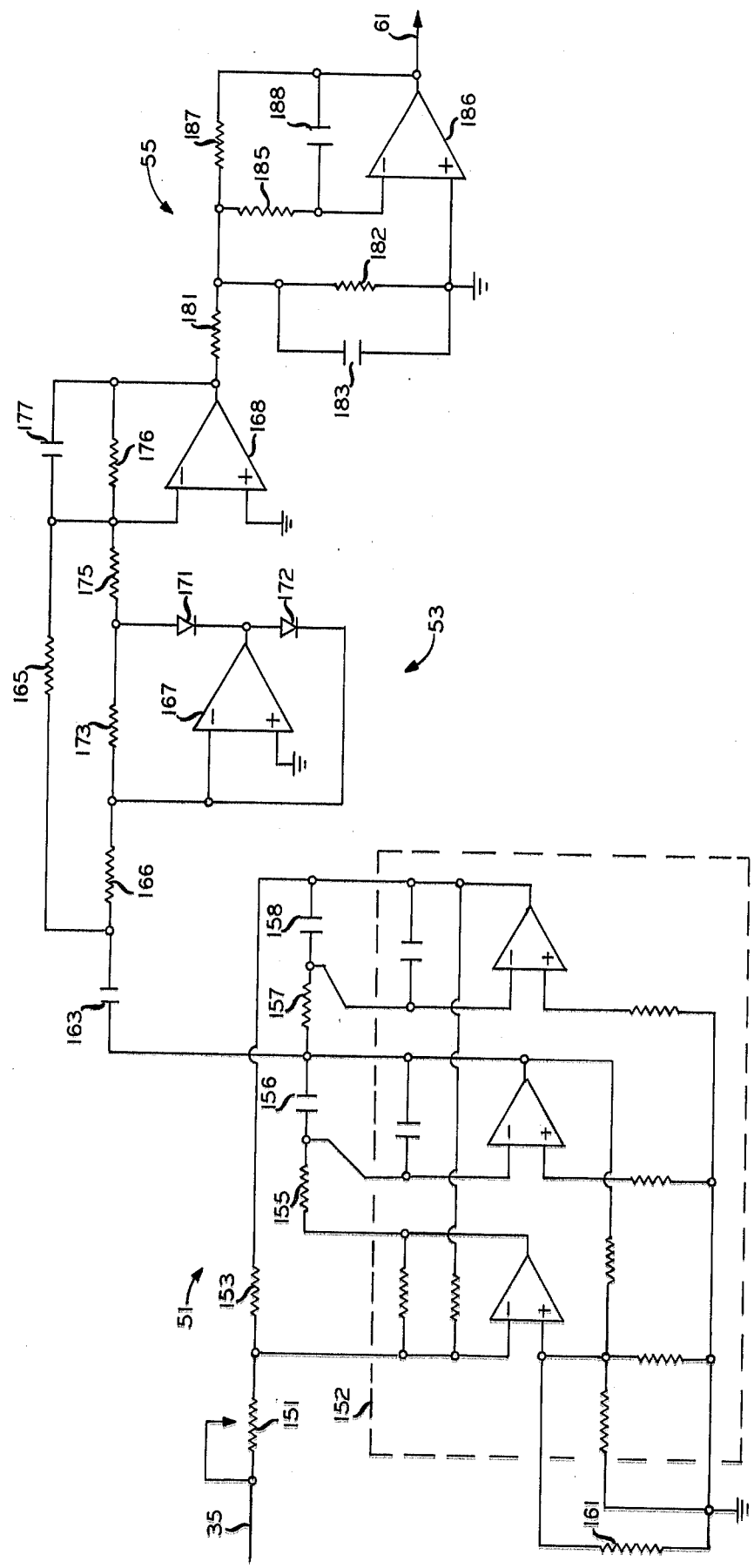
FIG. 5 is a schematic block diagram of a preferred tuned amplifier, full wave rectifier, and low band-pass amplifier for use in amplifying and demodulating detector signals in accordance with the invention.

A preferred tuned amplifier 51, full wave rectifier 53, and low band-pass amplifier 55 for use in amplifying and demodulating the detector signal 35 are illustrated by FIG. 5. Athough any suitable circuit can be utilized as the tuned amplifier 51, the presently preferred circuit illustrated employs an active filter circuit 152 as the basis of the tuned amplifier. The preferred active filter is a hybrid integrated circuit filter employing multiloop negative feedback which is tunable over a frequency range of DC to approximately 10 kHz by the addition of external resistors, capacitors, and other circuit components. The specific active filter 152 illustrated is a FS-60 Hybrid universal active filter available from Kinetic Technology Inc., Santa Clara, California. When such a device is employed connections to the numbered terminals thereof are as illustrated and as hereinafter described. It is to be understood, however, that other equivalent circuits combining filtering and amplification can be utilized.

The detector signal 35 is applied through a variable resistor 151 to terminal 6 of the ES-60 active filter 152. The variable resistor 151 is utilized for matching and proper scaling of detector circuits when a plurality of detectors are utilized in the analysis apparatus of the invention. Terminal 6 of the active filter 152 is in turn connected through a resistor 153 to terminal 7 thereof. Terminals 1 and 2 are connected through a resistor 155, terminals 2 and 12 are connected through a capacitor 156, terminals 12 and 10 are connected through a resistor 157, and terminals 10 and 7 are connected through a capacitor 158. In addition, terminal 8 of the FS-60 active filter 152 is connected through a resistor 161 to ground, and terminals 14 and 4 are connected to ground. The amplified and filtered output of the tuned amplifier 51 is applied from terminal 12 of the FS-60 circuit through a coupling capacitor 163 to the input of a full wave rectifier circuit 53. Since the FS-60 circuitry is not linear over its entire range, scaling of the circuitry is preferably used to maintain a range of outputs from the circuit within the range of 0 to about ±8.2 volts. Adjustment of the aperture of the line 26 (FIG. 1) can also be used to obtain proper voltage scaling for the FS-60 circuit and other circuits.

The signal arriving through the coupling capacitor 163 is applied through a resistor 165 to the inverting input of an operational amplifier 168 and is also applied through a resistor 166 to the inverting input of an operational amplifier 167. The noninverting inputs of amplifiers 167 and 168 are connected to ground. The output of the amplifier 167 is connected to the cathode of a diode 171 and to the anode of a diode 172. The cathode of the diode 172 is in turn connected to the inverting input of the amplifier 167, and the anode of the diode 171 is connected through a resistor 173 to the inverting input of the amplifier 167. The anode of the diode 171 is also connected through a resistor 175 to the inverting input of the operational amplifier 168. The output of the amplifier 168 is connected to the inverting input thereof through the parallel combination of a resistor 176 and a capacitor 177. In order to provide full wave rectification, the resistor 165, 166, and 173 each have substantially twice the resistance of the resistor 175.

The full wave rectified output of the amplifier 168 is applied through a resistor 181 to the low band-pass amplifier circuit 55. The terminal of the resistor 181 opposite its connection to the output of the amplifier 168 is connected through the parallel combination of a resistor 182 and a capacitor 183 to ground. This same terminal is also connected through a resistor 185 to the inverting input of an operational amplifier 186 and through a resistor 187 to the output of the operational amplifier 186. The output of the amplifier 186 is connected through a capacitor 188 to the inverting input thereof. The noninverting input of the amplifier 186 is connected to ground. The values of the various circuit components, particularly the resistor 182 and capacitor 183, are chosen so that frequencies higher than those desired to be observed in the scanning of a sample surface are attenuated while those low frequency variations which represent measured reflectance signals are delivered from the output of the amplifier 186 as a reflectance signal 61. As with the detector and preamplifier circuits, the tuned amplifier, full wave rectifier, and low band-pass amplifier circuits associated with each of a plurality of detectors are preferably as nearly the same as is practical. When an additional detector, such as a reference detector 28, is utilized the detector circuit, preamplifier circuit, tuned amplifier circuit, full wave rectifier circuit, and low band-pass circuit associated therewith can be the same as those employed with the detectors used to generate surface quality signals. If desired, however, other suitable circuitry sufficient to fulfill the less demanding requirements of surface reflection characterization associated with the reference detector 28 can be utilized.

Figure 6:
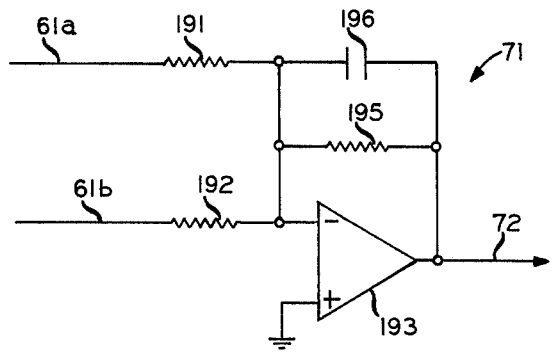
FIG. 6 is a schematic representation of a preferred reflectance summing circuit for use with the invention.

FIG. 6 illustrates a preferred circuit for use as the summing amplifier 71 of FIG. 2. Reflectance signals 61a and 61b are applied through respective, substantially equal, resistors 191 and 192 to the inverting input of an operational amplifier 193. The noninverting input of the amplifier 193 is connected to ground and the output of the amplifier 193 is connected to the inverting input thereof through the parallel combination of a resistor 195 and a capacitor 196. When the resistors 191 and 192 are equal, the output signal 72 of the amplifier 193 is proportional to and representative of the sum of the reflectance signals 61a and 61b. Application of additional reflectance signals through additional resistors equal in value to the resistors 191 and 192 would result in the additional signals so applied being additively represented in the output signal 72. Assignment of different values to different reflectance signals could be accomplished by alteration of the relative relationships between the resistors 191 and 192 or among various other resistors so employed.

Figure 7:
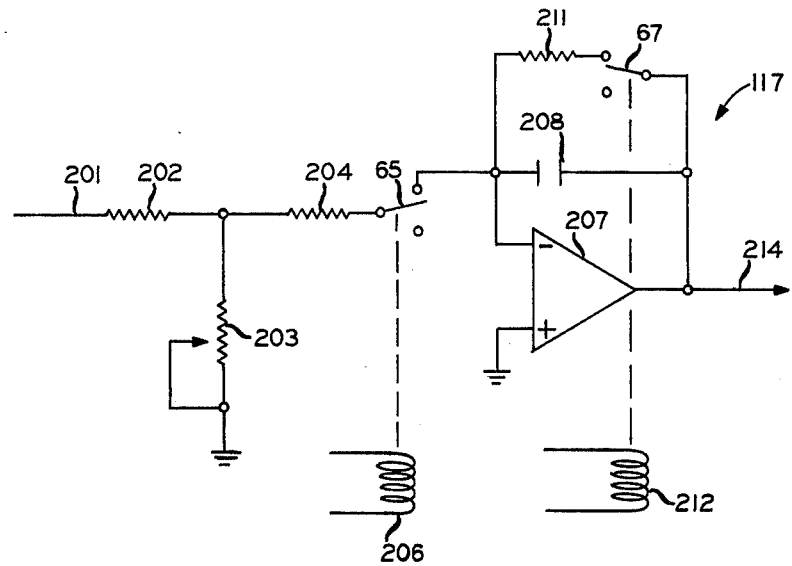
FIG. 7 is a schematic representation of a preferred integrator for use with the invention.

A preferred integrator 117 which can be used as integrator 111, 112, 113, 114, 115, or 116 or FIG. 2 is illustrated by FIG. 7. An input signal 201, which can be any signal responsive to one or more of the reflectance signals generated in response to the reflection of light from the surface of the sample being scanned, is applied through a resistor 202 and a variable resistor 203 to ground. In series combination, the resistors 202 and 203 provide a voltage divider circuit which, with adjustments of the resistor 203, can be used to scale the signal applied through the resistor 204 to the switch means 65. The switch 65 is automatically actuated by any suitable means such as a relay coil 206 which can be actuated in response to a command from a logic circuit 62 (FIG. 2). One of the two possible terminals which can be selected by the switching means 65 for connection with the resistor 204 is connected to the inverting input of an operational amplifier 207. The noninverting input of the operational amplifier 207 is connected to ground. The output of the amplifier 207 is connected through a capacitor 208 to the inverting input terminal thereof. A resistor 211 connected to the inverting input of the amplifier 207 can be connected by the switch means 67 to the output of the amplifier 207 when the switch is actuated by any suitable means such as a relay coil 212 which may, like the relay coil 206, be responsive to a signal from the logic circuitry 62. When switch means 65 is utilized to provide an input signal from the resistor 204 to the inverting input of the amplifier 207 and switch means 67 is used to prevent communication through the resistor 211 from the inverting input of the amplifier 207 to the output thereof, the illustrated circuit acts an an integrator to produce an output signal 214 which is representative of the integral of the signal 201 applied to the circuit. Disconnecting the resistor 204 from the inverting input of the amplifier 207 by opening the switch 65 will halt further integration and cause the then existing signal 214 to be maintained as the output of the amplifier 207. Closing of the switch means 67 to connect the output of the amplifier 207 through the resistor 211 to the inverting input thereof will cause the capacitor 208 to be discharged through the resistor 211 and will therefore result in resetting of the integrator circuit to an initial or zero position.

Figure 8:
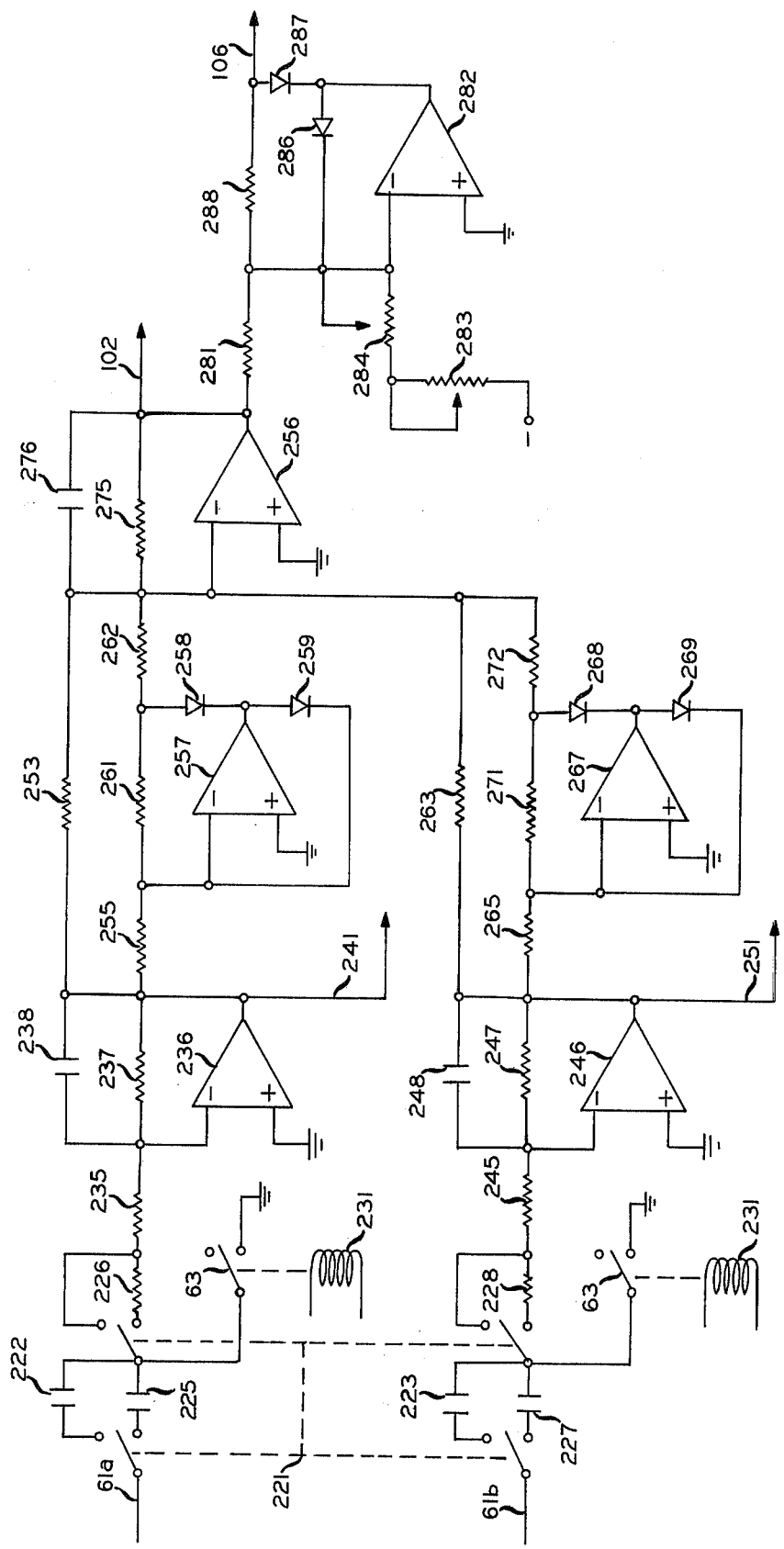
FIG. 8 is a schematic representation of a preferred additive differential signal generating circuit for use with the invention.

FIG. 8 illustrates a preferred circuit for use in generating a weighted total absolute value signal 106 in response to two reflectance signals 61a and 61b. A double pole double throw switch means 221 is utilized to select between capacitive coupling each of the signals 61a and 61b through one of a pair of capacitors 222 and 223 to the remainder of the circuit or capacitive-resistive coupling through a series combination of capacitor 225 and resistor 226 or capacitor 227 and resistor 228. Either of the capacitive coupling combinations preferably transmits only the low frequency variations in the instantaneous reflectance signals 61a and 61b to approximate the rate of change of each reflectance, thereby resulting in inputs to the circuits which are essentially derivatives of the instantaneous reflectance signals 61a and 61b. The switch means 63 associated with each coupling capacitor can be actuated by any suitable means such as an associated relay coil 231 responsive to the logic circuitry 62 (FIG. 2) to ground the capacitors 222, 223, 225, and 227 in order to initialize or zero the input capacitors before the start of each test measurement.

The capacitor coupled signal transmitted by the capacitor 222 or the series combination of the capacitor 225 and resistor 226 is applied through a resistor 235 to the inverting input of an operational amplifier 236. The noninverting input of the amplifier 236 is connected to ground. The output of the amplifier 236 is connected to the noninverting input thereof through the parallel combination of a resistor 237 and a capacitor 238. The action of the amplifier 236 and its associated resistive and capacitive elements is to provide a stabilized amplification of the derivative of the instantaneous reflectance signal 61a as an output signal 241 of the amplifier 236. In a similar manner, resistors 245 and 247 and a capacitor 248 having substantially the same values as respective resistors 235 and 237 and capacitor 238 are associated with an operational amplifier 246 having substantially the same characteristics as the operational amplifier 236 in order to produce an amplified derivative signal 251 representative of the derivative of the instantaneous reflectance signal 61b.

The derivative signal 241 is applied through a resistor 253 to the inverting input of an operational amplifier 256. The signal 241 is also applied through a resistor 255 to the inverting input of an operational amplifier 257. The noninverting input of the amplifier 257 is connected to ground. The output of the amplifier 257 is connected to the cathode of a diode 258 and to the anode of a diode 259. The cathode of the diode 259 is connected to the inverting input of the amplifier 257. The anode of the diode 258 is connected through a resistor 261 to the inverting input of the amplifier 257. The anode of the diode 258 is also connected to a resistor 262 to the inverting input of the amplifier 256. In order to provide full wave rectification of the signal 241, the resistors 253, 255, and 261 are each of substantially equal value and each have substantially twice the resistance of the resistor 262. In a similar manner, resistors 263, 265, 271, and 272 along with an operational amplifier 267 and diodes 268 and 269 provide for the basis for full wave rectification of the signal 251. The output of the operational amplifier 256 is connected by the parallel combination of a resistor 275 and a capacitor 276 to the inverting input thereof. The amplifier 256 operates as an adding amplifier so that the output signal received therefrom is a total absolute value signal 102. While the schematic block diagram of FIG. 2 illustrates an additional half wave rectification step in order to arrive at the total absolute value signal 102, use of substantially equal circuit components for the circuits which process the reflectance signals 61a and 61b respectively and use of the circuit illustrated by FIG. 8 will result in an output signal from the amplifier 256 which will be of a single polarity and which will not be altered by further half wave rectification.

In order to generate the weighted total absolute value signal 106, the total absolute value signal 102 is applied through a resistor 281 to the inverting input of an amplifier 282. In addition a bias signal of opposite polarity from the total absolute value signal 102 and of a magnitude determined by the settings of the variable resistors 283 and 284 connected between the inverting input of the operational amplifier 282 and a negative voltage source is applied to the inverting input of the amplifier 282. The noninverting input of the amplifier 282 is connected to ground. The output of the amplifier 282 is connected to the anode of a diode 286 and to the cathode of a diode 287. The cathode of a diode 286 is connected to the inverting input of the amplifier 282. The anode of the diode 287 is connected through a resistor 288 to the inverting input of the amplifier 282. The anode of the diode 287 also provides the half wave rectified weighted total absolute value signal 106 representative of the amount by which the total absolute value signal 102 exceeds the preselected bias signal magnitude.

Figure 9:
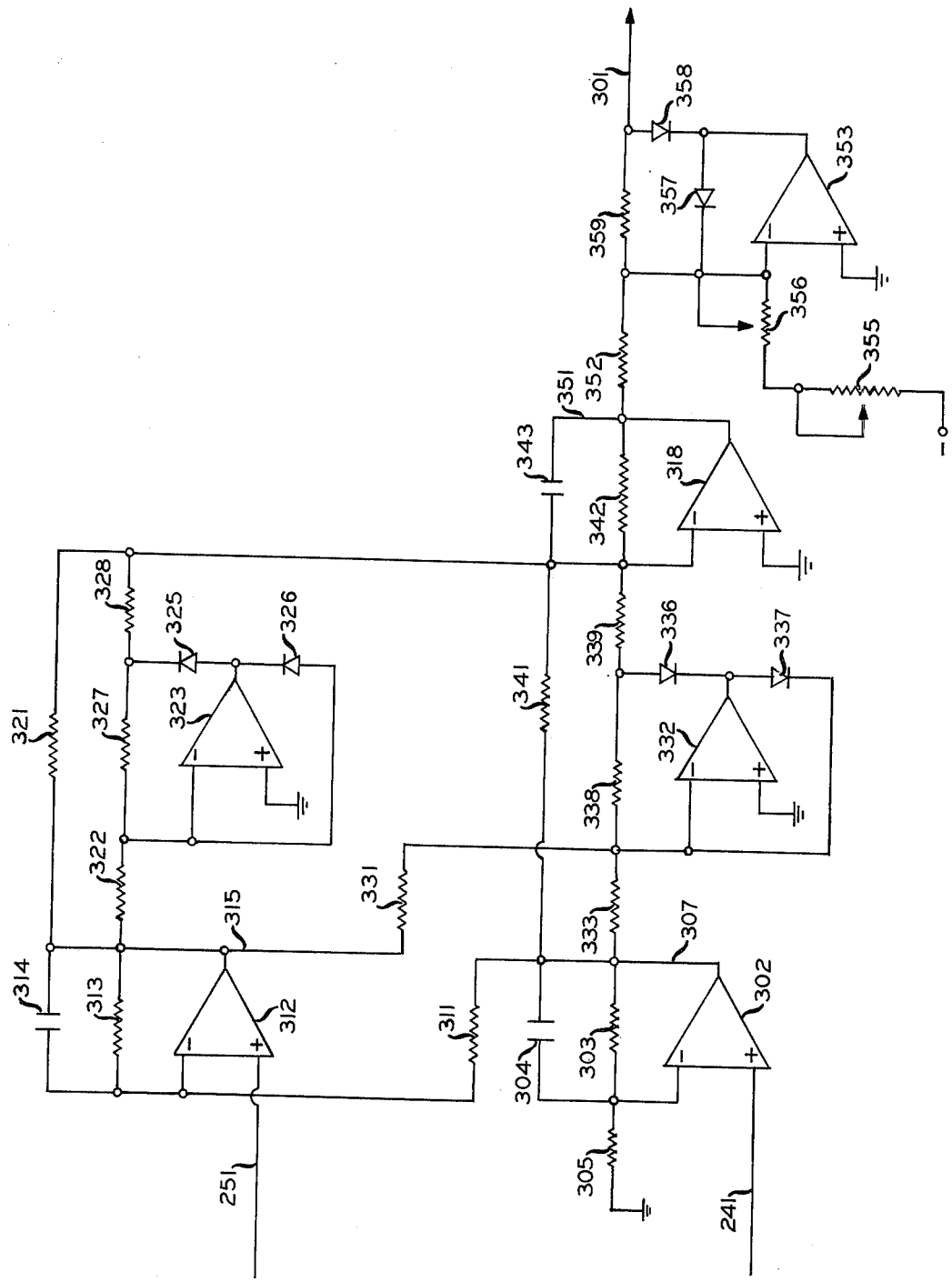
FIG. 9 is a schematic representation of a preferred subtractive differential signal generating circuit for use with the invention.

FIG. 9 illustrates a circuit by which a weighted discriminatory output signal 301 analogous to the weighted discriminatory output signal 89 discussed in conjunction with the description of FIG. 2 can be produced utilizing the differential signals 241 and 251 as inputs. While the full wave rectifiers 81 and 82, subtracting amplifier 83, and half wave rectifiers 85 and 87 illustrated by FIG. 2 can be implemented and utilized to produce the desired discriminatory signal and weighted discriminatory signal, the circuit of FIG. 9 implements the same signal conditioning techniques utilizing circuitry which has eliminated redundancy and has otherwise been simplified but which still generates the desired resultant signal. In the operation of the circuit of FIG. 9, the differential signal 241 is applied to the noninverting input of an operational amplifier 302. The output of the amplifier 302 is connected to the inverting input thereof by the parallel combination of a resistor 303 and a capacitor 304. The inverting input of the amplifier 302 is connected to ground through a resistor 305. The output signal 307 of the operational amplifier 302 is equal to approximately twice the value of the differential signal 241. The output signal 307 from the amplifier 302 is applied through a resistor 311 to the inverting input of an operational amplifier 312. The differential signal 251 is applied to the noninverting input of the operational amplifier 312. The output of the amplifier 312 is connected to the inverting input thereof by the parallel combination of the resistor 313 and a capacitor 314. The output signal 315 from the operational amplifier 312 is equal to approximately twice the value of signal 251 less twice the value of signal 241. Signal 315 is applied through a resistor 321 to the inverting input of an operational amplifier 318. Signal 315 is also applied through a resistor 322 to the inverting input of an operational amplifier 323. The noninverting input of the amplifier 323 is connected to ground. The output of the amplifier 323 is connected to the anode of a diode 325 and to the cathode of a diode 326. The anode of the diode 326 is connected to the inverting input of the amplifier 323. The cathode of the diode 325 is connected through a resistor 327 to the inverting input of the amplifier 323. The cathode of the diode 325 is also connected through a resistor 328 to the inverting input of the amplifier 318. The signal 315 is also applied through a resistor 331 to the inverting input of an operational amplifier 332. The signal 307 is applied through a resistor 333 to the inverting input of the amplifier 332. The noninverting input of the amplifier 332 is connected to ground. The output of the amplifier 332 is connected to the cathode of a diode 336 and to the anode of a diode 337. The cathode of the diode 337 is connected to the inverting input of the amplifier 332. The anode of the diode 336 is connected through a resistor 338 to the inverting input of the amplifier 332. The anode of the diode 336 is also connected through a resistor 339 to the inverting input of the amplifier 318. In addition, the output signal 307 from the amplifier 302 is applied through a resistor 241 to the inverting input of the amplifier 318. The output of the amplifier 318 is connected to the inverting input thereof through the parallel combination of a resistor 242 and a capacitor 243. In order to achieve the desired output signal, resistors 321, 322, 327, 328, 331, 338, 339, and 341 are all of substantially equal value, each having approximately twice the resistance of the resistor 333. Utilizing the circuit illustrated with such a relationship among the named resistors, the output signal 351 of the amplifier 318 will be equal to $$|C + D| - |D - C|$$

where C represents the noninverting input to the amplifier 302 or signal 241 and where D represents the noninverting input to the amplifier 312 or signal 251.

The signal 351 is then applied through a resistor 352 to an inverting input of an operational amplifier 353. A bias signal determined by the value of the variable resistors 355 and 356 is applied from a negative voltage supply source through the variable resistor 355 and 356 to the inverting input of the amplifier 353. The noninverting input of the amplifier 353 is connected to ground. The output of the amplifier 353 is connected to the anode of a diode 357 and to the cathode of a diode 358. The cathode of a diode 357 is connected to the inverting input of the amplifier 353. The anode of the diode 358 is connected through a resistor 359 to the inverting input of the amplifier 353. The weighted discriminatory signal 301 is provided at the anode of the diode 358 and will be representative of the amount by which the smaller of the signals 241 or 251 exceeds the preselected bias signal when the signals 241 and 251 are of the same polarity and will be equal to zero when the signals 241 and 251 are of opposite polarity. By disconnecting the bias input applied to the inverting input terminal of the amplifier 353 through the resistor 355 and 356, the same circuit can be employed to output an unweighted discriminatory signal which is equal in magnitude to the smaller of the differential signals 241 and 251 when those signals of the same polarity and which is equal to zero when signals 241 and 251 are of opposite polarity.

While the invention has been described herein in conjunction with presently preferred analog circuitry, the method and apparatus herein disclosed can be adapted by those skilled in the art to other electrical analog or digital electronic implementations to implementations employing pneumatic, hydraulic, mechanical, or other similar systems as well as combinations of electrical analog, digital electronic, pneumatic, hydraulic, mechanical, or other implementations.

When the method and apparatus of the invention are to be implemented utilizing the specific circuits illustrated herein, preferred components which can be utilized in the construction of the circuits illustrated by FIGS. 4–9 are as follows:

FIG. 4

| | |
|---|---|
| Photo sensitive detector 131 | Model FS-617 photo sensitive field effect transistor Teledyne Crystalonics Cambridge, Mass. |
| Operational amplifier 141 | Model 48K Analog Devices Inc. Norwood, Mass. |
| Resistor 132 | 1 K ohm |
| Resistor 137 | 100 M |
| Resistor 138 | 8.2 K |
| Resistor 142 | 100 K |
| Resistor 146 | 1 M |
| Resistor 147 | 2.2 K |
| Resistor 148 | 4.7 K |
| Capacitors 135 & 136 | 100 μ |
| Capacitor 145 | 0.0018 μ |
| Diode | PM-10 |

FIG. 5

| | |
|---|---|
| Tuned amplifier 152 | Model FS-60 Hybrid universal active filter Kinetic Technology Inc. Santa Clara, California |
| Operational amplifiers 167 & 168 | Model 40K Analog Devices Inc. |
| Operational amplifiers 186 | Model 48K Analog Devices Inc. |
| Variable resistor 151 | 100 K |
| Resistors 153 & 155 | 50 K |
| Resistor 157 | 150 K |
| Resistor 161 | 4.7 K |
| Resistors 165, 166 & 173 | 20 K |
| Resistors 175 & 182 | 10 K |
| Resistor 176 | 39 K |
| Resistors 181, 185 & 187 | 200 K |
| Capacitors 156 & 158 | 0.01 μ |
| Capacitor 163 | 1 μ |
| Capacitor 177 | 0.47 μ |
| Capacitor 183 | 0.8 μ |
| Capacitor 188 | 0.0082 μ |
| Diodes 171 & 172 | 1N914 |

FIG. 6

| | |
|---|---|
| Operational amplifier 193 | Model 40K Analog Devices Inc. |
| Resistors 191 & 192 | 20 K |
| Resistor 195 | 10 K |
| Capacitor 196 | 1 μ |

FIG. 7

| | |
|---|---|
| Operational amplifier 207 | Model 40K Analog Devices Inc. |
| Resistor 202 | 27 K |
| Variable resistor 203 | 5 K |
| Resistor 204 | 1 M |
| Resistor 211 | 100 ohms |
| Capacitor 208 | 1 μ |

FIG. 8

| | |
|---|---|
| Operational amplifiers 236, 246, 256, 257, 267 & 282 | Model 40K Analog Devices Inc. |
| Resistors 226 & 228 | 10 K |
| Resistors 235 & 245 | 8.2 K |
| Resistors 237 & 247 | 2.2 M |
| Resistors 253, 255, 261, 263, 265, 271, 281 & 288 | 20 K |
| Resistors 262 & 272 | 10 K |
| Resistor 275 | 18.2 K |

-continued

| | |
|---|---|
| Variable Resistor 283 | 100 K |
| Variable Resistor 284 | 100 K |
| Capacitors 222 & 223 | 2 to 100 μ* |
| Capacitors 225 & 227 | 2 to 100 μ* |
| Capacitors 238 & 248 | 0.0082 μ |
| Capacitor 276 | 0.517 μ |
| Diodes 258, 259, 268, 269, 286 & 287 | 1N914 |

*Various values can be used depending on whether derivative or AC amplifier effect is desired. Values of 2μ provide a derivative effect. Values of 100μ provide an AC amplifier effect.

FIG. 9

| | |
|---|---|
| Operational amplifiers 302, 312 318, 323, 332 & 353 | Model 40K Analog Devices Inc. |
| Resistors 303, 305, 313, 321, 322, 327, 328, 331, 338, 339 & 341 | 20 K |
| Resistor 333 | 10 K |
| Resistor 342 | 18.2 K |
| Resistor 352 | 50 K |
| Variable Resistor 355 | 100 K |
| Variable Resistor 356 | 100 K |
| Resistor 359 | 100 K |
| Capacitors 304 & 314 | 0.0082 μ |
| Capacitor 343 | 0.517 μ |
| Diodes 325, 326, 336, 337, 357 & 358 | 1N914 |

In addition, suitable output devices illustrated by FIG. 2 include the following:

| | |
|---|---|
| Multiplexer 68 | Model 3705 Fairchild Semiconductor Inc. Mt. View, California |
| Time base divider 121 | Model 424 K high accuracy wideband multiplier (wired as a divider in accordance with manufacturer's published brochure) Analog Devices, Inc. Norwood, Mass. |

Positive and negative voltage sources suitable for use with circuitry constructed in accordance with FIGS. 4–9 and using the above-identified circuit components are voltages of +15 volts for positive voltage sources and −15 volts for negative voltage sources. In order to provide more accurate operation of the Model 40K and 48K amplifier, external trim potentiometers are preferably added in accordance with the manufacturer's recommendations.

In the actual testing of the surface characteristics of knitted and test dyed sleeves, the apparatus of the invention implemented utilizing the circuits illustrated by FIGS. 4–9, use of the method and apparatus of the invention showed good overall correlation with the conclusions of professional human evaluators but exhibited a considerable improvement and reproducibility over that of subjective human evaluations.

In addition to using two or more detectors in a generally straight line array to view the sample surface, it is within the scope of the invention to use a triangular or rectangular array to discriminate in favor of or against variation of certain widths and lengths. Many other similar modifications such as the use of individual lenses for the various detectors, use of light transmitting fiber optic materials in lieu of one or more lenses, and similar modifications to the sample viewing system may be advantageous in some applications. The signal electronics likewise may be modified to provide equivalent surface quality signal generation. The description provided herein has been primarily in terms of the value of which a specific signal may be representative. In this regard it is noted that this representation may be linear or nonlinear, of like or inverted polarity, of an expanded or reduced scale, or may otherwise vary from a direct representation of a physical value. Use of any such system of representation which permits a reproducible correlation between a signal and the value which it represents is possible within the scope of the invention. These and other reasonable variations and modifications by those skilled in the art are considered to be within the scope of the invention and of the depended claims thereto.

THAT WHICH IS CLAIMED IS:

1. Apparatus comprising:

light source means for illuminating at least a portion of a surface;

detector assembly means for directing reflected light from said surface to a plurality of detector means for producing a plurality of reflectance signals responsive to the reflected light impinging thereon, said detector means being located within said detector assembly means, said detector assembly means being supported in a fixed position relative to said light source means;

drive means for effecting relative motion between said detector assembly means and said surface to provide scanning of said surface by said detector means; and means for generating, in response to said plurality of reflectance signals, at least one surface quality signal responsive to the reflective characteristics of said surface;

wherein said detector assembly means comprises a lens and wherein the operative surface of each said detector means is located at the focal plane of said lens, said plurality of detector means being positioned in a preselected array to provide substantially simultaneous detection of reflected light from a plurality of preselected locations past which relative movement of said surface is accomplished during scanning of said surface; wherein said preselected locations comprise a substantially straight line positioned generally perpendicular to the direction of relative motion between the detector assembly means and said surface during scanning of said surface;

wherein there are two said detector means and wherein said means for generating said at least one surface quality signal comprises:

differentiating means associated with each said detector means for differentiating each said reflectance signal to produce a differential signal representative of the rate of change of its associated reflectance signal; and discriminator means for generating, in response to said differential signals, a discriminatory signal which is proportional to the magnitude of the smaller of said differential signals when said differential signals are of the same polarity and which is equal to zero when said differential signals are of opposite polarity.

2. Apparatus in accordance with claim 1 wherein said means for generating said at least one surface quality signal additionally comprises integrating means for integrating said discriminatory signal over the period of time during which scanning of said surface is being accomplished.

3. Apparatus in accordance with claim 2 wherein said means for generating said at least one surface quality signal additionally comprises first bias rectifier means for generating a weighted discriminatory signal representative of the amount by which said discriminatory signal exceeds a preselected constant bias signal.

4. Apparatus in accordance with claim 3 wherein said means for generating at least one surface quality signal additionally comprises integrating means for integrating said weighted discriminatory signal over the period of time during which scanning of said surface is being accomplished.

5. Apparatus in accordance with claim 3 wherein said means for generating said at least surface quality signal additionally comprises full ware rectifier means associated with each said differentiating amplifier means for generating an absolute value signal representative of the absolute value of each said differential signal.

6. Apparatus in accordance with claim 5 wherein said means for generating at least one surface quality signal additionally comprises adding means for generating a summed signal representative of the sum of said absolute value signals.

7. Apparatus in accordance with claim 6 wherein said means for generating at least one surface quality signal additionally comprises integrating means for integrating said summed signal over the period of time during which scanning of said surface is being accomplished.

8. Apparatus in accordance with claim 6 wherein said means for generating said at least one surface quality signal additionally comprises bias rectifier means for generating a weighted summed signal representative of the amount by which said summed signal exceeds a preselected constant bias signal.

9. Apparatus in accordance with claim 8 wherein said means for generating at least one surface quality signal additionally comprises integrating means for integrating said weighted summed signal over the period of time during which scanning of said surface is being accomplished.

10. Apparatus comprising:
light source means for illuminating at least a portion of a surface;
detector assembly means for directing reflected light from said surface to a plurality of detector means for producing a plurality of reflectance signals responsive to the reflected light impinging thereon, said detector means being located within said detector assembly means, said detector assembly means being supported in a fixed position relative to said light source means;
drive means for effecting relative motion between said detector assembly means and said surface to provide scanning of said surface by said detector means; and
means for generating, in response to said plurality of reflectance signals, at least one surface quality signal responsive to the reflective characteristics of said surface;
said means for generating said at least one surface quality signal comprises:
differentiating means associated with each said detector means for differentiating each said reflectance signal to produce a differential signal representative of the rate of change of its associated reflectance signal; and
full wave rectifier means associated with each said differentiating means for generating an absolute value signal representative of the absolute value of each said differential signal.

11. Apparatus in accordance with claim 10 wherein said means for generating at least one surface quality signal additionally comprises adding means for generating a summed signal representative of the sum of said absolute value signals.

12. Apparatus in accordance with claim 11 wherein said means for generating at least one surface quality signal additionally comprises integrating means for integrating said summed signal over the period of time during which scanning of said surface is being accomplished.

13. Apparatus in accordance with claim 11 wherein said means for generating said at least one surface quality signal additionally comprises bias rectifier means for generating a weighted summed signal representative of the amount by which said summed signal exceeds a preselected constant bias signal.

14. Apparatus in accordance with claim 13 wherein said means for generating at least one surface quality signal additionally comprises integrating means for integrating said weighted summed signal over the period of time during which scanning of said surface is being accomplished.

15. A method for analyzing the quality of a surface, said method comprising the steps of:
illuminating said surface with a modulated light source;
detecting reflection from said surface with at least one detector means by scanning said surface to generate a detector signal associated with each said detector means;
demodulating each said detector signal to produce a reflectance signal associated with each said detector means; and
generating, in response to at least one said reflectance signal, a surface quality signal representative of the reflective characteristics of said surface;
wherein generating said surface quality signal comprises:
differentiating each said reflectance signal to obtain a differential signal representative of the rate of change of its associated reflectance signal; and
generating an absolute value signal representative of the absolute value of at least one said differential signal.

16. A method in accordance with claim 15 wherein generating said surface quality signal additionally comprises:
integrating said absolute value signal over the period of time during which said surface is being scanned to produce an integrated absolute value signal; and
dividing said integrated absolute value signal by a signal representative of the length of scanning time to produce a surface quality signal.

17. A method in accordance with claim 15 wherein generating said surface quality signal additionally comprises generating a weighted absolute value signal representative of the amount by which said absolute value signal exceeds a preselected constant bias signal.

18. A method in accordance with claim 17 wherein generating said surface quality signal additionally comprises:
integrating said weighted absolute value signal over the period of time during which said surface is being scanned to produce an integrated weighted absolute value signal; and dividing said integrated weighted absolute value signal by a signal representative of the length of scanning time to produce a surface quality signal.

19. A method in accordance with claim 15 wherein said surface is scanned by a plurality of said detector means and wherein generating said surface quality signal further comprises:
generating a total absolute value signal representative of the sum of the thus-generated absolute value signals.

20. A method in accordance with claim 19 wherein generating said surface quality signal additionally comprises:
integrating said total absolute value signal over the period of time during which said surface is being scanned to produce an integrated total absolute value signal; and
dividing said integrated total absolute value signal by a signal representative of the length of scanning time to produce a surface quality signal.

21. A method in accordance with claim 19 wherein generating said surface quality signal additionally comprises generating a weighted total absolute value signal representative of the amount by which said total absolute value signal exceeds a preselected constant signal.

22. A method in accordance with claim 21 wherein generating said surface quality signal additionally comprises:
integrating said weighted total absolute value signal over the period of time during which said surface is being scanned to produce an integrated weighted total absolute value signal; and
dividing said integrated weighted total absolute value signal by a signal representative of the length of scanning time to produce a surface quality signal.

23. A method in accordance with claim 15 additionally comprising positioning a plurality of detector means in a detector array to provide substantially simultaneous detection of reflected light from a plurality of preselected locations past which relative movement of said surface is accomplished during scanning of said surface.

24. A method in accordance with claim 23 comprising positioning two detector means to provide substantially simultaneous detection of reflected light from two locations, said two locations defining a generally straight line positioned generally perpendicular to the scanning direction.

25. A method for analyzing the quality of a surface, said method comprising the steps of:
illuminating said surface with a modulated light source;
positioning a plurality of detector means in a detector array to provide substantially simultaneous detection of reflected light from a plurality of preselected locations past which relative movement of said surface is accomplished during scanning of said surface;
detecting reflection from said surface with said plurality of detector means by scanning said surface to generate a detector signal associated with each said detector means;
demodulating each said detector signal to produce a reflectance signal associated with each said detector means; and
generating, in response to at least one said reflectance signal, a surface quality signal representative of the reflective characteristics of said surface;
wherein generating said surface quality signal comprises:
differentiating each reflectance signal to obtain a differential signal representative of the rate of change of its associated reflectance signal; and
generating, in response to said differential signals, a discriminatory signal which is proportional to the magnitude of the smallest of said differential signals having a like polarity when at least a preselected majority of said differential signals are of said like polarity, and which is equal to zero when less than a preselected majority of said differential signals are of like polarity.

26. A method in accordance with claim 25 wherein said preselected locations comprise a generally straight line positioned generally perpendicular to the scanning direction.

27. A method in accordance with claim 25 wherein generating said surface quality signal additionally comprises:
integrating said discriminatory signal over the period of time during which said surface is being scanned to produce an integrated discriminatory signal; and
dividing said integrated discriminatory signal by a signal representative of the length of scanning time to produce a surface quality signal.

28. A method in accordance with claim 27 wherein said preselected locations comprise a generally straight line positioned generally perpendicular to the scanning direction.

29. A method in accordance with claim 25 wherein generating said surface quality signal additionally comprises generating a weighted discriminatory signal representative of the amount by which said discriminatory signal exceeds a preselected constant bias signal.

30. A method in accordance with claim 29 wherein said preselected locations comprise a generally straight line positioned generally perpendicular to the scanning direction.

31. A method in accordance with claim 29 wherein generating said surface quality signal additionally comprises:
integrating said weighted discriminatory signal over the period of time during which said surface is being scanned to produce an integrated weighted discriminatory signal; and
dividing said integrated weighted discriminatory signal by a signal representative of the length of scanning time to produce a surface quality signal.

32. A method in accordance with claim 31 wherein said preselected locations comprise a generally straight line positioned generally perpendicular to the scanning direction.

33. A method for analyzing the quality of a surface, said method comprising the steps of:
illuminating said surface with a modulated light source;
detector means to provide substantially simultaneous detection of reflected light from two locations, said two locations defining a generally straight line positioned generally perpendicular to the scanning direction;
detecting reflection from said surface with said two detector means by scanning said surface to generate a detector signal associated with each said detector means;

demodulating each said detector signal to produce a reflectance signal associated with each said detector means; and generating, in response to at least one said reflectance signal, a surface quality signal representative of the reflective characteristics of said surface;

wherein generating said surface quality signal comprises:

differentiating each reflectance signal to obtain a differential signal representative of the rate of change of its associated reflectance signal; and generating, in response to said differential signals, a discriminatory signal which is proportional to the magnitude of the smaller of said differential signals when said differential signals are of the same polarity and which is equal to zero when said differential signals are of opposite polarity.

34. A method in accordance with claim 33 wherein generating said surface quality signal additionally comprises:

integrating said discriminatory signal over the period of time during which said surface is being scanned to produce an integrated discriminatory signal; and dividing said integrated discriminatory signal by a signal representative of the length of scanning time to produce a surface quality signal.

35. A method in accordance with claim 33 wherein generating said surface quality signal additionally comprises generating a weighted discriminatory signal representative of the amount by which said discriminatory signal exceeds a preselected constant bias signal.

36. A method in accordance with claim 35 wherein generating said surface quality signal additionally comprises:

integrating said weighted discriminatory signal over the period of time during which said surface is being scanned to produce an integrated weighted discriminatory signal; and dividing said integrated weighted discriminatory signal by a signal representative of the length of scanning time to produce a surface quality signal.

37. A method for analyzing the quality of a surface, said method comprising the steps of:

illuminating said surface with a modulated light source;

detector means to provide substantially simultaneous detection of reflected light from two locations, said two locations defining a generally straight line positioned generally perpendicular to the scanning direction;

detecting reflection from said surface with said two detector means by scanning said surface to generate a detector signal associated with each said detector means;

demodulating each said detector signal to produce a reflectance signal associated with each said detector means; and generating, in response to at least one said reflectance signal, a surface quality signal representative of the reflective characteristics of said surface;

wherein generating said surface quality signal comprises:

differentiating each said reflectance signal to obtain a differential signal representative of the rate of change of its associated reflectance signal;

generating a first signal representative of the sum of said differential signals;

generating a second signal representative of the difference between said differential signals;

generating a third signal representative of the absolute value of said first signal;

generating a fourth signal representative of the absolute value of said second signal;

generating a fifth signal representative of the difference between said third signal and said fourth signal; and generating a sixth signal which is of proportional magnitude to said fifth signal when the magnitude of said third signal exceeds the magnitude of said fourth signal and which is equal to zero when the magnitude of said fourth signal exceeds the magnitude of said third signal.

38. A method in accordance with claim 37 wherein generating said surface quality signal additionally comprises:

integrating said sixth signal signal over the period of time during which said surface is being scanned to produce a seventh signal; and dividing said seventh signal by a signal representative of the length of scanning time to produce a surface quality signal.

39. A method in accordance with claim 37 additionally comprising generating a weighted signal representative of the amount by which said sixth signal exceeds a preselected constant bias signal.

40. A method in accordance with claim 39 wherein generating said surface quality signal additionally comprises:

integrating said weighted signal over the period of time during which said surface is being scanned to produce an integrated weighted signal; and dividing said integrated weighted signal by a signal representative of the length of scanning time to produce a surface quality signal.

41. A method for analyzing the quality of a surface, said method comprising the steps of:

illuminating said surface;

detecting reflection from said surface by scanning said surface with a plurality of detector means to generate a reflectance signal associated with each said detector means; and generating, in response to two or more of said reflectance signals, at least one surface quality signal representative of the reflective characteristics of said surface;

wherein generating said surface quality signal comprises:

differentiating each said reflectance signal to obtain a differential signal representative of the rate of change of its associated reflectance signal;

generating an absolute value signal representative of the absolute value of each said differential signal; and generating a total absolute value signal representative of the sum of the thus-generated absolute value signals.

42. A method in accordance with claim 41 wherein generating said surface quality signal additionally comprises:

integrating said total absolute value signal over the period of time during which said surface is being scanned to produce an integrated total absolute value signal; and dividing said integrated total absolute value signal by a signal representative of the length of scanning time to produce a surface quality signal.

43. A method in accordance with claim 41 wherein generating said surface quality signal additionally comprises generating a weighted total absolute value signal representative of the amount by which said total absolute value signal exceeds a preselected constant signal.

44. A method in accordance with claim 43 wherein generating said surface quality signal additionally comprises:
integrating said weighted total absolute value signal over the period of time during which said surface is being scanned to produce an integrated weighted total absolute value signal; and
dividing said integrated weighted total absolute value signal by a signal representative of the length of scanning time to produce a surface quality signal.

45. A method in accordance with claim 41 additionally comprising positioning said plurality of detector means in a detector array to provide substantially simultaneous detection of reflected light from a plurality of preselected locations past which relative movement of said surface is accomplished during scanning of said surface.

46. A method for analyzing the quality of a surface, said method comprising the steps of:
illuminating said surface;
positioning said plurality of detector means in a detector array to provide substantially simultaneous detection of reflected light from a plurality of preselected locations past which relative movement of said surface is accomplished during scanning of said surface;
detecting reflection from said surface by scanning said surface with said plurality of detector means to generate a reflectance signal associated with each said detector means; and
generating, in response to two or more of said reflectance signals, at least one surface quality signal representative of the reflective characteristics of said surface;
wherein generating said surface quality signal comprises:
differentiating each reflectance signal to obtain a differential signal representative of the rate of change of its associated reflectance signal; and
generating, in response to said differential signals, a discriminatory signal which is proportional to the magnitude of the smallest of said differential signals having a like polarity when at least a preselected majority of said differential signals are of said like polarity, and which is equal to zero when less than a preselected majority of said differential signals are of like polarity.

47. A method in accordance with claim 46 wherein said preselected locations comprise a generally straight line positioned generally perpendicular to the scanning direction.

48. A method in accordance with claim 46 wherein generating said surface quality signal additionally comprises:
integrating said discriminatory signal over the period of time during which said surface is being scanned to produce an integrated discriminatory signal; and
dividing said integrated discriminatory signal by a signal representative of the length of scanning time to produce a surface quality signal.

49. A method in accordance with claim 48 wherein said preselected locations comprise a generally straight line positioned generally perpendicular to the scanning direction.

50. A method in accordance with claim 46 wherein generating said surface quality signal additionally comprises generating a weighted discriminatory signal representative of the amount by which said discriminatory signal exceeds a preselected constant bias signal.

51. A method in accordance with claim 50 wherein said preselected locations comprise a generally straight line positioned generally perpendicular to the scanning direction.

52. A method in accordance with claim 50 wherein generating said surface quality signal additionally comprises:
integrating said weighted discriminatory signal over the period of time during which said surface is being scanned to produce an integrated weighted discriminatory signal; and
dividing said integrated weighted discriminatory signal by a signal representative of the length of scanning time to produce a surface quality signal.

53. A method in accordance with claim 52 wherein said preselected locations comprise a generally straight line positioned generally perpendicular to the scanning direction.

54. A method for analyzing the quality of a surface, said method comprising the steps of:
illuminating said surface;
positioning two detector means to provide substantially simultaneous detection of reflected light from two locations, said two locations defining a generally straight line positioned generally perpendicular to the scanning direction;
detecting reflection from said surface by scanning said surface with said two detector means to generate a reflectance signal associated with each said detector means; and
generating, in response to two or more of said reflectance signals, at least one surface quality signal representative of the reflective characteristics of said surface;
wherein generating said surface quality signal comprises:
differentiating each reflectance signal to obtain a differential signal representative of the rate of change of its associated reflectance signal; and
generating, in response to said differential signals, a discriminatory signal which is proportional to the magnitude of the smaller of said differential signals when said differential signals are of the same polarity and which is equal to zero when said differential signals are of opposite polarity.

55. A method in accordance with claim 54 wherein generating said surface quality signal additionally comprises:
integrating said discriminatory signal over the period of time during which said surface is being scanned to produce an integrated discriminatory signal; and
dividing said integrated discriminatory signal by a signal representative of the length of scanning time to produce a surface quality signal.

56. A method in accordance with claim 54 wherein generating said surface quality signal additionally comprises generating a weighted discriminatory signal representative of the amount by which said discriminatory signal exceeds a preselected constant bias signal.

57. A method in accordance with claim 56 wherein generating said surface quality signal additionally comprises:

integrating said weighted discriminatory signal over the period of time during which said surface is being scanned to produce an integrated weighted discriminatory signal; and dividing said integrated weighted discriminatory signal by a signal representative of the length of scanning time to produce a surface quality signal.

58. A method for analyzing the quality of a surface, said method comprising the steps of:

illuminating said surface;

positioning two detector means to provide substantially simultaneous detection of reflected light from two locations, said two locations defining a generally straight line positioned generally perpendicular to the scanning direction;

detecting reflection from said surface by scanning said surface with said two detector means to generate a reflectance signal associated with each said detector means; and generating, in response to two or more of said reflectance signals, at least one surface quality signal representative of the reflective characteristics of said surface;

wherein generating said surface quality signal comprises:

differentiating each said reflectance signal to obtain a differential signal representative of the rate of change of its associated reflectance signal;

generating a first signal representative of the sum of said differential signals;

generating a second signal representative of the difference between said differential signals;

generating a third signal representative of the absolute value of said first signal;

generating a fourth signal representative of the absolute value of said second signal;

generating a fifth signal representative of the difference between said third signal and said fourth signal; and generating a sixth signal which is of proportional magnitude to said fifth signal when the magnitude of said third signal exceeds the magnitude of said fourth signal and which is equal to zero when the magnitude of said fourth signal exceeds the magnitude of said third signal.

59. A method in accordance with claim 58 wherein generating said surface quality signal additionally comprises:

integrating said sixth signal over the period of time during which said surface is being scanned to produce a seventh signal; and dividing said seventh signal by a signal representative of the length of scanning time to produce a surface quality signal.

60. A method in accordance with claim 58 additionally comprising generating a weighted signal representative of the amount by which said sixth signal exceeds a preselected constant bias signal.

61. A method in accordance with claim 60 wherein generating said surface quality signal additionally comprises:

integrating said weighted signal over the period of time during which said surface is being scanned to produce an integrated weighted signal; and dividing said integrated weighted signal by a signal representative of the length of scanning time to produce a surface quality signal.

* * * * *